United States Patent
Shaltis

(10) Patent No.: US 9,937,325 B2
(45) Date of Patent: Apr. 10, 2018

(54) CATHETER SYSTEM

(71) Applicant: Covidien LP, Mansfield, MA (US)

(72) Inventor: Phillip Shaltis, Sharon, MA (US)

(73) Assignee: Covidien LP, Mansfield, MA (US)

( * ) Notice: Subject to any disclaimer, the term of this patent is extended or adjusted under 35 U.S.C. 154(b) by 24 days.

(21) Appl. No.: 14/150,253

(22) Filed: Jan. 8, 2014

(65) Prior Publication Data

US 2015/0190615 A1 Jul. 9, 2015

(51) Int. Cl.
*A61M 25/01* (2006.01)
*A61M 25/09* (2006.01)
*A61M 25/00* (2006.01)

(52) U.S. Cl.
CPC ........ *A61M 25/0147* (2013.01); *A61M 25/09* (2013.01); *A61M 25/0054* (2013.01); *A61M 2025/0058* (2013.01); *A61M 2025/0081* (2013.01); *A61M 2025/015* (2013.01); *A61M 2025/0186* (2013.01); *A61M 2025/09008* (2013.01); *A61M 2025/09125* (2013.01)

(58) Field of Classification Search
CPC .. A61M 2025/0058; A61M 2025/0081; A61M 2025/015; A61M 2025/0186; A61M 2025/09008; A61M 2025/09125; A61M 25/0054; A61M 25/0147; A61M 25/09
See application file for complete search history.

(56) References Cited

U.S. PATENT DOCUMENTS

| | | | |
|---|---|---|---|
| 2,498,692 A * | 2/1950 | Mains ................ | A61M 25/10 604/915 |
| 5,046,497 A | 9/1991 | Millar | |
| 5,171,233 A * | 12/1992 | Amplatz et al. ............. | 604/540 |
| 5,755,695 A | 5/1998 | Erickson et al. | |
| 6,126,649 A * | 10/2000 | VanTassel ......... | A61M 25/0147 604/528 |
| 7,682,365 B2 | 3/2010 | Guinan | |
| 8,137,336 B2 | 3/2012 | Ostrovsky et al. | |
| 2002/0138094 A1* | 9/2002 | Borillo et al. ............... | 606/200 |

(Continued)

FOREIGN PATENT DOCUMENTS

| | | |
|---|---|---|
| CN | 1245225 C | 3/2006 |
| EP | 0371486 A1 | 6/1990 |

(Continued)

OTHER PUBLICATIONS

Extended European Search Report from counterpart European Patent Application No. 1510154.1, dated May 20, 2015, 9 pp.

(Continued)

*Primary Examiner* — Imani Hayman
(74) *Attorney, Agent, or Firm* — Shumaker & Sieffert, P.A.

(57) ABSTRACT

A catheter system includes an elongate catheter having a lumen extending at least partially therethrough, and a leading catheter end segment, a guidewire positionable within the lumen of the catheter, and fastening structure supported adjacent the leading catheter end segment. The guidewire and the catheter are adapted for relative movement. The fastening structure is dimensioned to selectively engage the guidewire to secure the guidewire with respect to the leading catheter end segment such that movement of the guidewire causes deflection of the leading end segment with respect to the longitudinal axis.

22 Claims, 12 Drawing Sheets

(56) References Cited

U.S. PATENT DOCUMENTS

| | | | |
|---|---|---|---|
| 2004/0133130 A1* | 7/2004 | Ferry | A61M 25/0127 600/585 |
| 2005/0131343 A1 | 6/2005 | Abrams et al. | |
| 2005/0165466 A1 | 7/2005 | Morris et al. | |
| 2006/0069323 A1* | 3/2006 | Elkins et al. | 600/585 |
| 2007/0244550 A1 | 10/2007 | Eidenschink | |
| 2008/0015625 A1* | 1/2008 | Ventura et al. | 606/191 |
| 2008/0114390 A1 | 5/2008 | Guinan | |
| 2008/0262432 A1 | 10/2008 | Miller | |
| 2009/0062789 A1 | 3/2009 | Rioux et al. | |
| 2009/0124978 A1 | 5/2009 | Abrams et al. | |
| 2009/0182268 A1* | 7/2009 | Thielen | A61M 25/0138 604/95.04 |
| 2011/0270169 A1 | 11/2011 | Gardeski et al. | |
| 2012/0078232 A1 | 3/2012 | Schulting | |
| 2014/0214057 A1* | 7/2014 | Piccagli | A61B 17/320725 606/159 |

FOREIGN PATENT DOCUMENTS

| | | |
|---|---|---|
| EP | 1297860 A1 | 4/2003 |
| WO | WO00/62852 A1 | 10/2000 |

OTHER PUBLICATIONS

Notification of the First Office Action, and translation thereof, from counterpart Chinese Application No. 201510091438.X, dated Feb. 24, 2017, 19 pp.

Notification of Second Office Action, and English translation thereof, from counterpart Chinese Application No. 201510091438.X, dated Nov. 16, 2017, 15 pp.

* cited by examiner

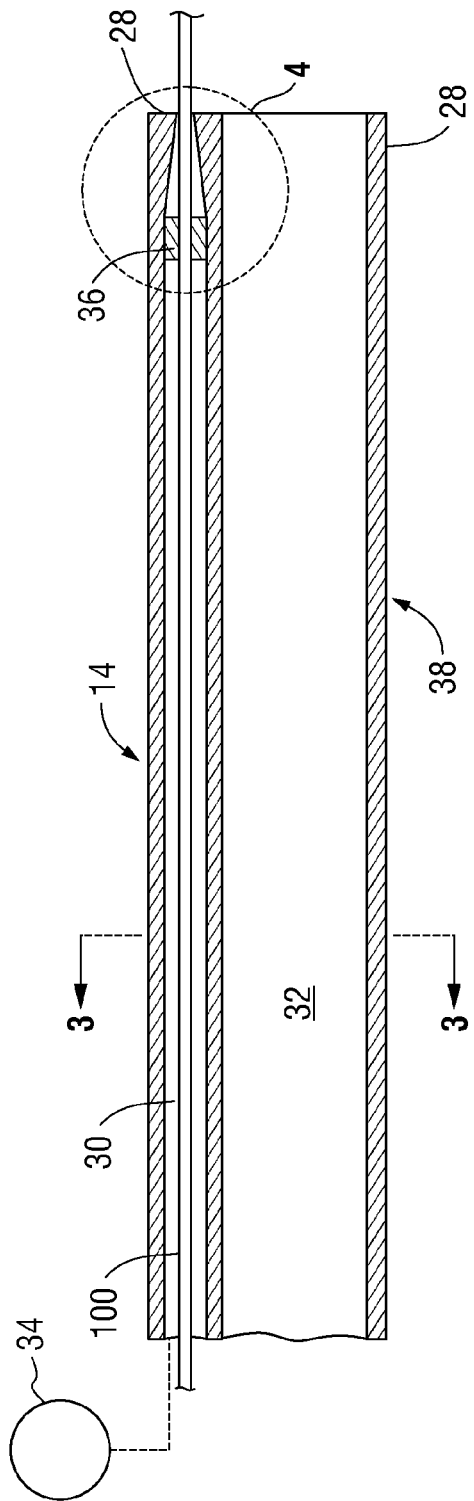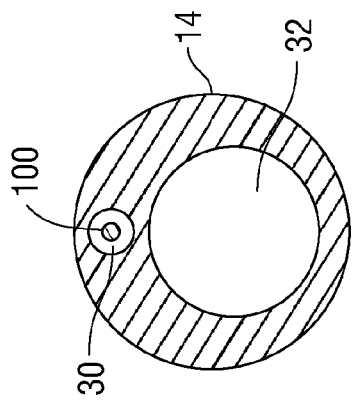
FIG. 2
FIG. 3

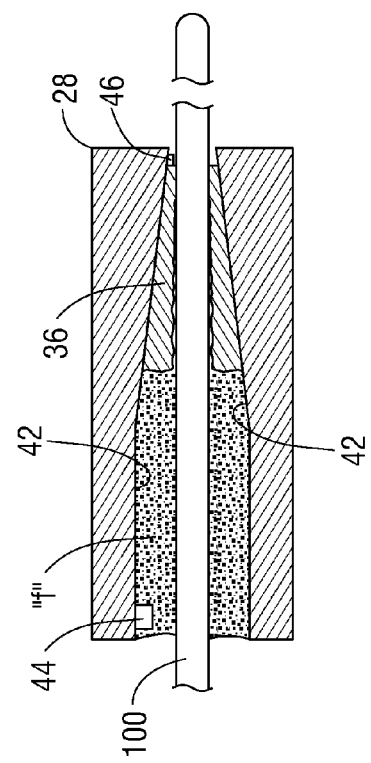
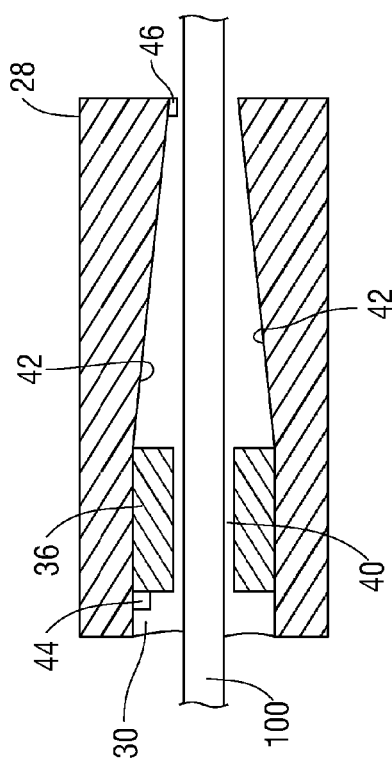
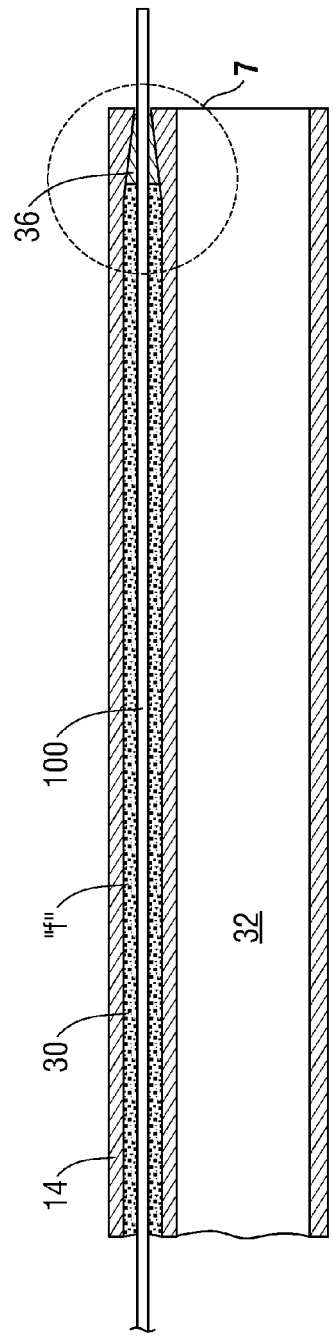

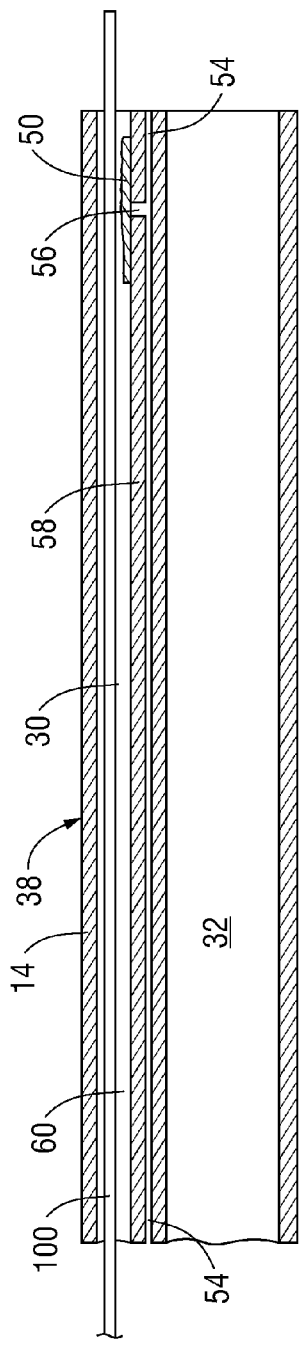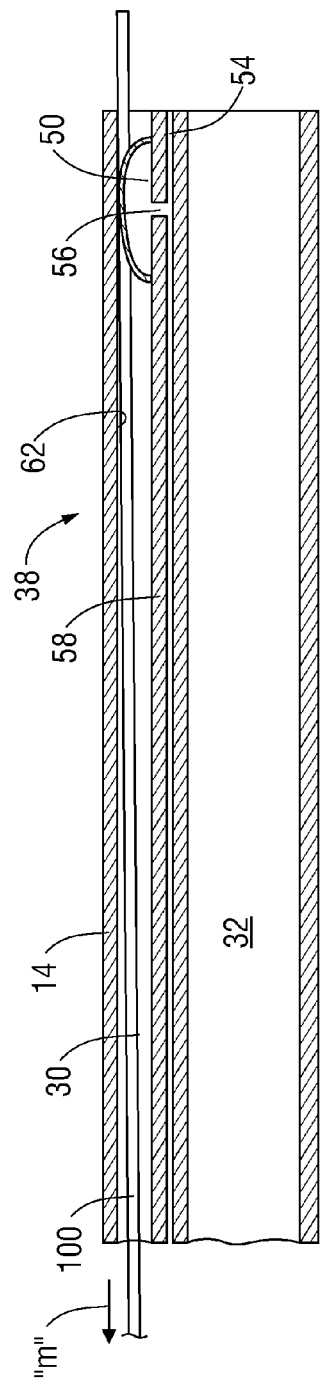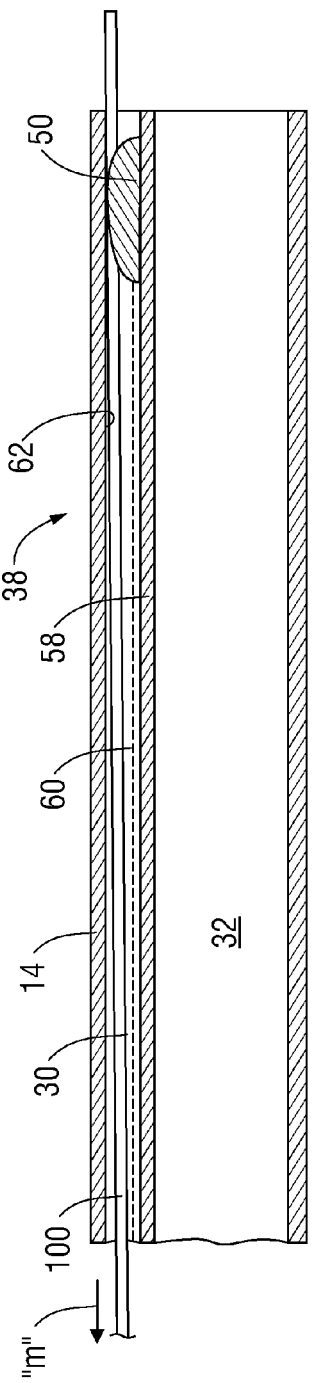

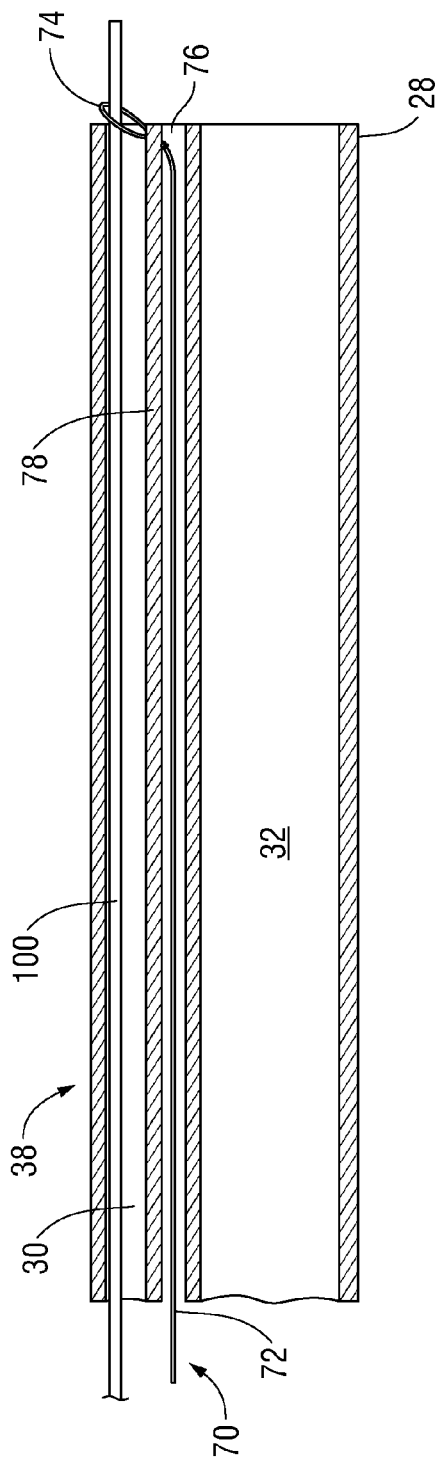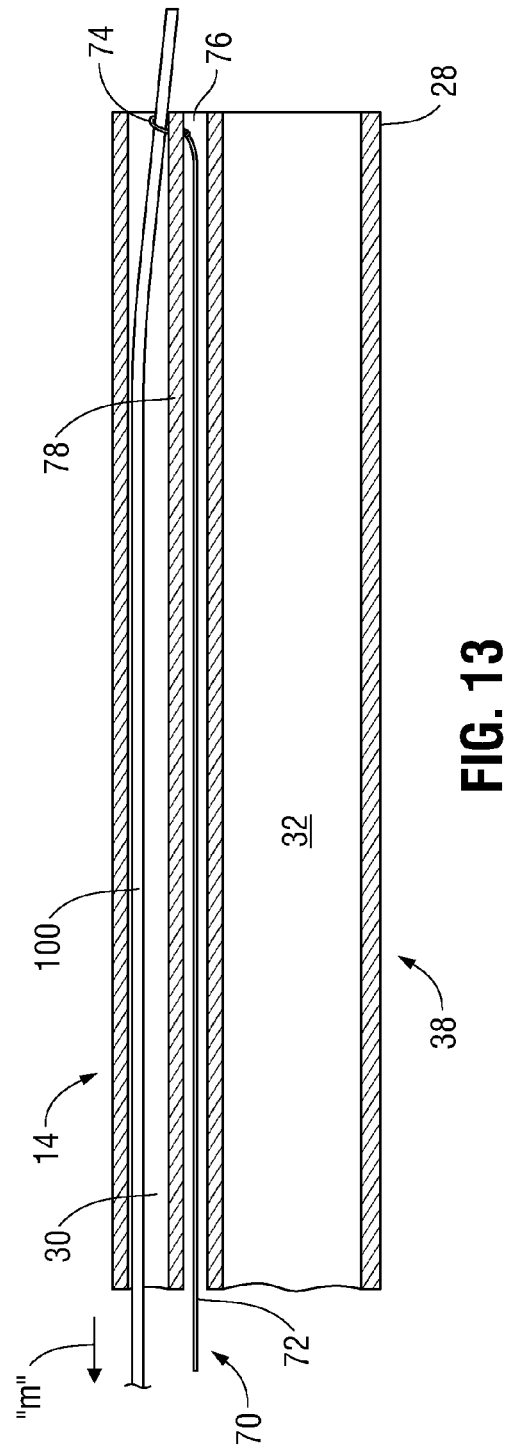

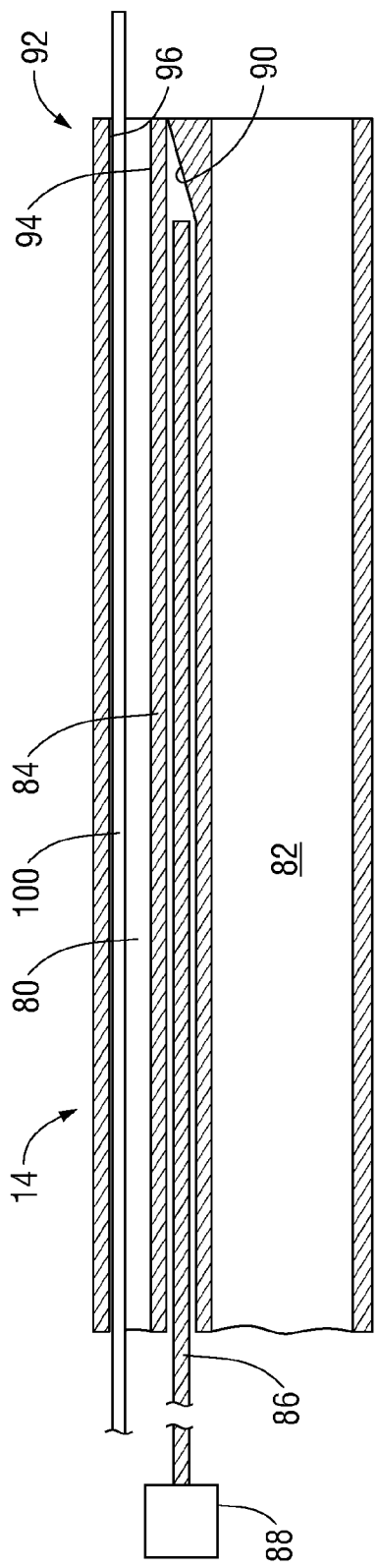
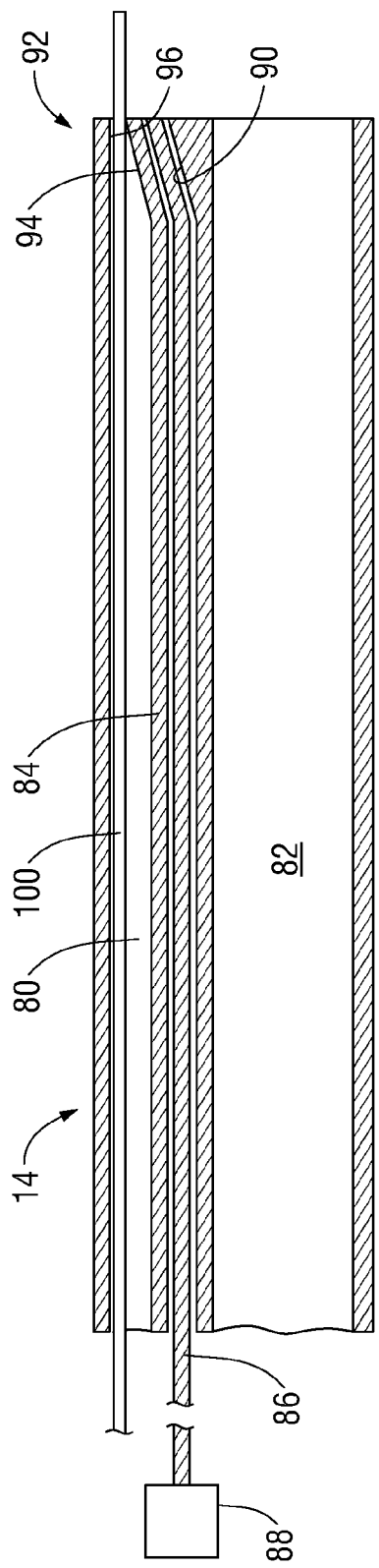
FIG. 14
FIG. 15

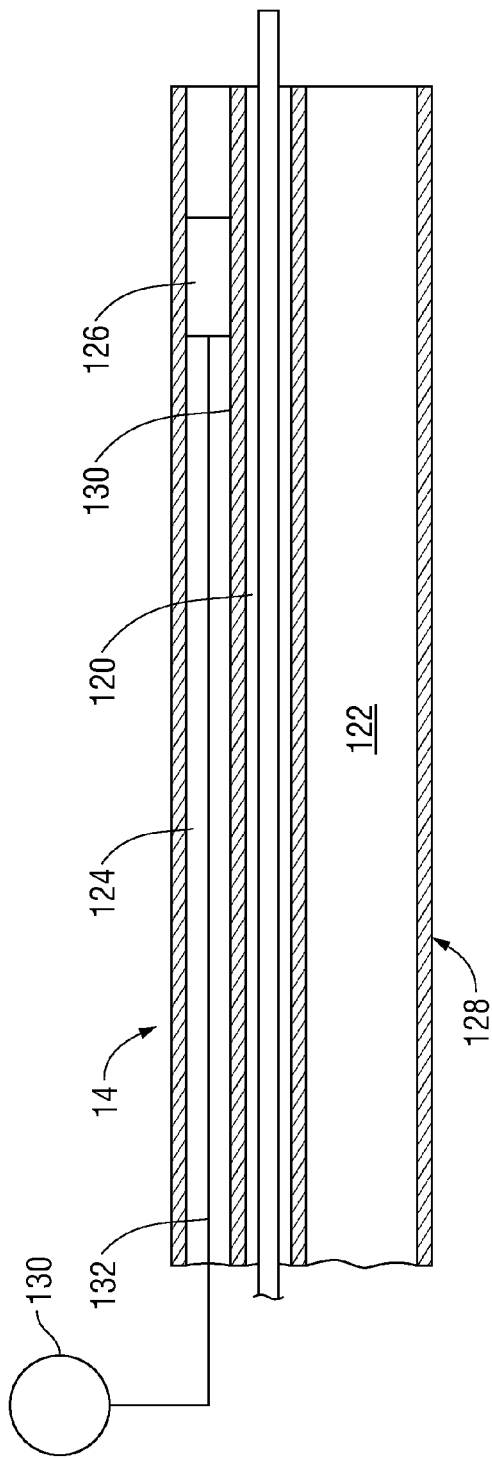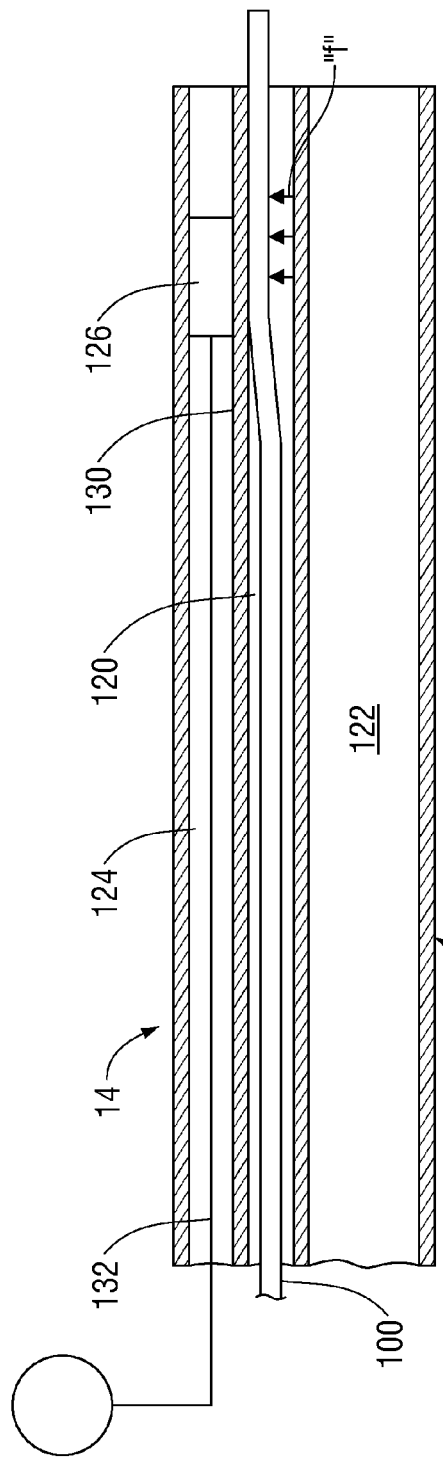

CATHETER SYSTEM

BACKGROUND

1. Technical Field

The present disclosure relates generally to medical systems and methods and, more particularly, relates to a steerable catheter system for use in an intravascular procedure.

2. Description of Related Art

Catheters are well known in the art. A catheter generally consists of an elongated, flexible tubular body defining at least one lumen extending therethrough. Catheters may be tracked along a previously positioned guidewire in the vasculature. The lumen provides a conduit for delivery of instrumentation or material to or from the body, or for the delivery of medical devices to a treatment site. Catheters may incorporate steering mechanisms permitting the clinician to deflect or manipulate the leading end of the catheter to navigate the often tortuous path of the vasculature. However, the steering mechanisms generally increase the cross-sectional dimension of the catheter, thus limiting the use of the catheters in certain procedures.

SUMMARY

The present disclosure is directed to improvements in steerable catheters. The catheter or medical system disclosed herein incorporates various mechanisms that engage a conventional guidewire with the leading end segment of a catheter. Once engaged the guidewire is manipulated to deflect the leading end segment of the catheter. Manipulation of the leading catheter end segment provides a low profile and selectively steerable catheter system for advancement within the vasculature.

In embodiments, a catheter system includes an elongate catheter defining a longitudinal axis having a lumen extending at least partially therethrough and a leading catheter end segment, a guidewire positionable within the lumen of the catheter, and a fastening structure supported adjacent the leading catheter end segment. The guidewire and the catheter are adapted for relative movement. The fastening structure is dimensioned to selectively engage the guidewire to secure the guidewire with respect to the leading catheter end segment such that movement of the guidewire causes deflection of the leading end segment with respect to the longitudinal axis.

The catheter may include a clamp adjacent the leading catheter end segment. The clamp is movable between a first position corresponding to the release condition of the guidewire and a second position corresponding to the secured condition of the guidewire where the clamp engages the guidewire in the lumen in secured relation therewith. In embodiments, the clamp is at least partially disposed within the lumen of the catheter when in the secured condition of the guidewire relative to the catheter. In embodiments, the clamp is a grommet defining a passage for reception of the guidewire. The grommet may be at least partially compressible to engage the guidewire upon movement to the actuated position. In embodiments, the grommet is adapted to move within the lumen from a first longitudinal position to a second longitudinal position in response to introduction of fluids within the lumen. The catheter may include internal tapered surfaces adjacent the lumen with the tapered surfaces cooperating with the grommet during movement thereof to the second longitudinal position to compress the grommet onto the guidewire. A source of pressurized fluids may be in fluid communication with the lumen.

In embodiments, the catheter includes at least one expandable member within the lumen. The at least one expandable member is adapted to transition between an initial condition corresponding to the release condition of the guidewire and an expanded condition corresponding to the secured condition of the guidewire in which the at least one expandable member engages the guidewire in secured relation therewith. The at least one expandable member may be a balloon member. In embodiments, the catheter includes an inflation tube extending through the lumen in fluid communication with the balloon member. Alternatively, the catheter defines a second lumen, which is an inflation lumen, and is in fluid communication with the balloon member.

In embodiments, a filament member extends along the catheter and defines a loop segment. The loop segment is dimensioned to receive the guidewire to secure the guidewire relative to the catheter to establish the secured condition of the guidewire relative to the catheter. The loop segment may include a lasso.

In embodiments, the catheter includes a device lumen dimensioned for reception of an interventional device.

In embodiments, the catheter includes a second lumen and a drive disposed within the second lumen. The drive is adapted for longitudinal movement within the second lumen from a first longitudinal position to a second longitudinal position to cause deflection of a wall surface of the first-mentioned lumen such that the wall surface engages the guidewire in secured relation thereby achieving the secured condition of the guidewire. The catheter may define an internally tapered surface adjacent the leading end thereof and at least partially defining the second lumen. The drive element may deflect towards the first-mentioned lumen upon traversing the tapered surface to cause deflection of the wall surface to drive the guidewire against an opposed internal wall surface of the first lumen.

In embodiments, the guidewire may be adapted for one of rotational or radial movement relative to the catheter to cause deflection of the leading catheter end segment.

In embodiments, the catheter may include first and second lumens and the leading catheter end segment having first and second catheter sections. First and second guidewires are positionable within the first and second lumens of the catheter. Each of the first and second guidewires is adapted for relative movement within the respective first and second lumens. First fastening structure is dimensioned to selectively engage the first guidewire to secure the first guidewire with respect to the first catheter section such that movement of the first guidewire causes deflection of the first catheter section and second fastening structure is dimensioned to selectively engage the second guidewire to secure the second guidewire with respect to the second catheter section such that movement of the second guidewire causes deflection of the second catheter section. The first catheter section may be adapted to deflect in a first radial direction with respect to the longitudinal axis and the second catheter section may be adapted to deflect in a second radial direction with respect to the longitudinal axis. The first radial direction may be different from the second radial direction.

In embodiments, the fastening structure and the guidewire each include ferromagnetic material. The fastening structure may include an electromagnet selectively activated by an electric current.

In embodiments, the guidewire includes a looped segment, and the catheter includes at least one detent depending into the lumen. The detent is positioned to engage the looped segment of the guidewire to secure the guidewire with respect to the leading catheter end segment.

In embodiments, the leading catheter end segment includes locking structure of predefined geometry within the lumen and the guidewire includes a locking element. The locking element is adapted to move between release and secured conditions with respect to the leading catheter end segment through relative rotation of the guidewire and the leading catheter end segment about the longitudinal axis.

In embodiments, a catheter system includes an elongate catheter having a lumen extending at least partially therethrough and a leading catheter end segment, a guidewire positionable within the lumen of the catheter and fastening structure supported adjacent the leading catheter end segment. The fastening structure is movable between initial and actuated positions thereof corresponding to respective release and coupled conditions of the guidewire relative to the leading catheter end segment. In the release condition, the guidewire and the catheter are capable of relative longitudinal movement. In the coupled condition, the guidewire and the leading catheter end segment are secured such that longitudinal movement of the guidewire causes deflection of the leading catheter end segment with respect to the longitudinal axis.

A medical method is also disclosed. The method includes introducing a guidewire within vasculature of a subject; advancing a catheter along the guidewire; securing the guidewire adjacent a leading end segment of the catheter; and manipulating the guidewire to cause deflection of the leading end segment of the catheter. Securing the guidewire may include selectively securing and releasing the guidewire relative to the leading end segment of the catheter. Securing the guidewire may be performed subsequent to advancing the catheter. The method may further include performing an interventional procedure. Performing the interventional procedure includes introducing a medical interventional device within the catheter.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2 is a side cross sectional view of the leading catheter end segment of the catheter of the catheter system of FIG. 1;

FIG. 3 is a cross-sectional view of the catheter taken along the lines 3-3 of FIG. 2;

FIG. 4 is an enlarged view of the area of isolation designated in FIG. 3 illustrating the grommet positioned within the guidewire lumen of the catheter and in a first position;

FIG. 6 is a side cross-sectional view similar to the view of FIG. 2 illustrating the grommet in a second position securing the guidewire relative to the leading catheter end segment;

FIG. 7 is an enlarged view of the area of isolation 7 designated in FIG. 6 illustrating the grommet in the second position;

FIG. 9 is a side cross-sectional view of an embodiment of the catheter incorporating an expandable member in the guidewire lumen and in an initial condition;

FIG. 10 is a view similar to the view of FIG. 9 illustrating the expandable member in an expanded condition securing the guidewire relative to the leading catheter end segment;

FIG. 11 is a side cross-sectional view of an alternate embodiment of the catheter of FIGS. 9-10, incorporating a separate inflation tube extending through the guidewire lumen;

FIG. 12 is a side cross-sectional view of an embodiment of the catheter incorporating a filament loop adjacent the guidewire lumen;

FIG. 13 is a view similar to the view of FIG. 12 illustrating the filament loop securing the guidewire relative to the leading catheter end segment;

FIG. 14 is a side cross-sectional view of an embodiment of the catheter member incorporating a drive member with the drive member in a first position corresponding to a release condition of the guidewire;

FIG. 15 is a view similar to the view of FIG. 14 illustrating the drive member in a second position corresponding to a secured condition of the guidewire;

FIG. 16 is a side cross-sectional view of another embodiment of the catheter member incorporating an electromagnet in an initial condition corresponding to a release condition of the guidewire;

FIG. 17 is a view similar to the view of FIG. 16 illustrating the electromagnet in an actuated condition corresponding to a secured condition of the guidewire;

DETAILED DESCRIPTION

In the following description, the term "proximal" refers to the end of the system extending outside the body closest to the clinician. The term "distal" or "leading" refers to the end or segment of the system remote from the clinician.

The system of the present disclosure has particular application in neurovascular procedures, but may also be used in any interventional, diagnostic, and/or therapeutic procedure including coronary vascular, peripheral vascular and gastrointestinal applications.

The system includes a catheter and a guidewire. The catheter may have various mechanisms adapted to selectively engage the guidewire along a leading catheter end segment of the catheter, and, in some embodiments along various longitudinal locations along the leading catheter end segment. In embodiments, the guidewire is introduced into the vasculature and the catheter is advanced along the guidewire. Thereafter, the catheter is coupled to the guidewire adjacent the leading end segment. In this engaged relation, the guidewire may be retracted or rotated causing the leading catheter end segment to deflect or bend to a desired orientation. The guidewire provides steering capabilities to the catheter system without necessitating the use of pull wires or other mechanisms within the catheter. This may significantly reduce the profile of the catheter and maximize the size of a second or device lumen, which receives an interventional device.

Figure 1:
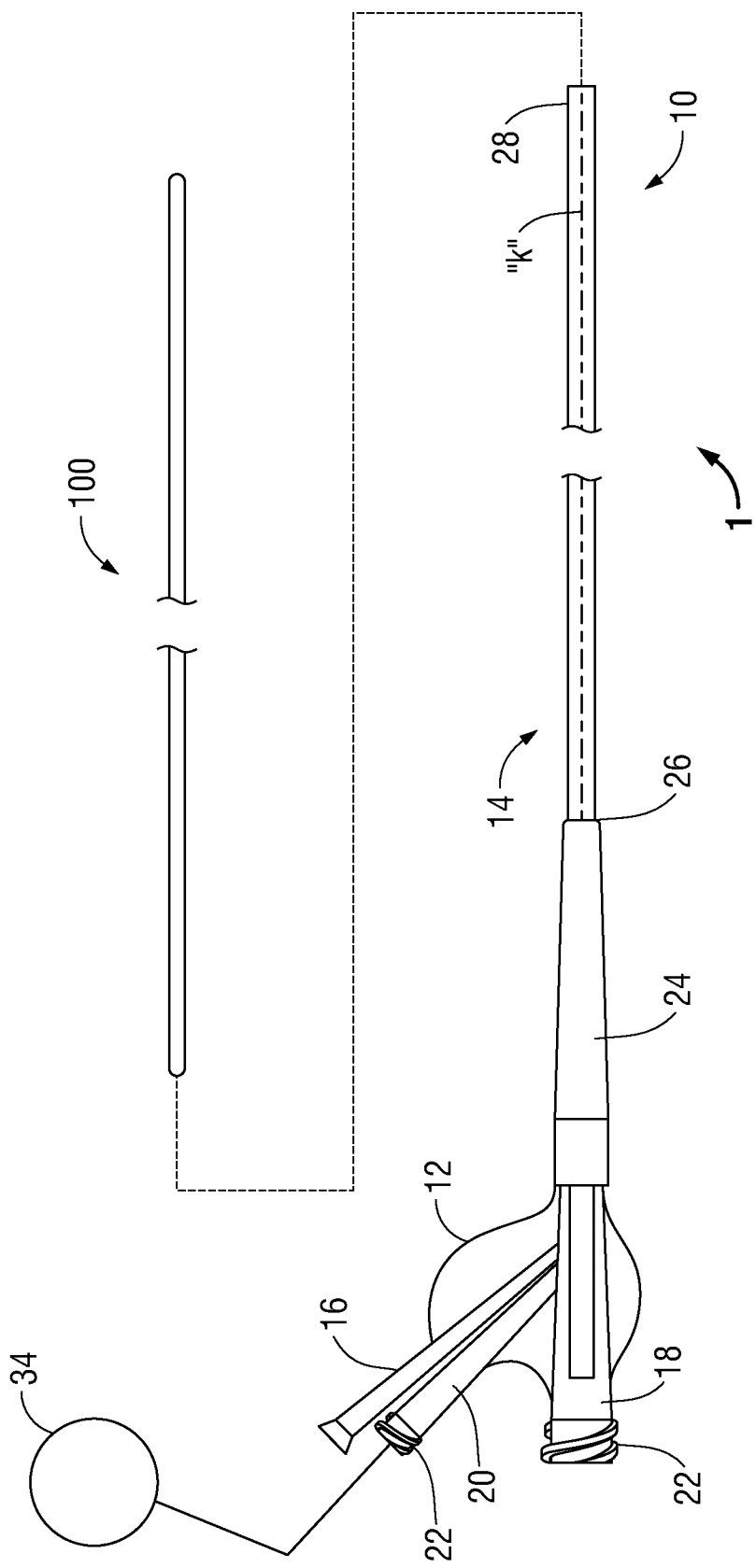
FIG. 1 illustrates a view of the catheter system in accordance with the principles of the present disclosure illustrating a catheter and a guidewire positionable within the catheter.

Referring now to FIG. 1, the system 1 of the present disclosure is illustrated and includes a catheter 10 and a guidewire 100. The catheter 10 may be a microcatheter adapted for use in neurovascular procedures. The catheter 10 includes a catheter hub 12 and an elongated catheter member 14 extending from the catheter hub 12, and defining a longitudinal axis "k". The catheter hub 12 may include a first port 16 for introduction of a guidewire and a second port 18 for reception of an interventional device. The catheter hub 12 also may include a third port 20 for introduction of fluids used in conjunction with the various mechanisms adapted to selectively engage the guidewire. Any of the first, second or third ports 16, 18, 20 may have a threaded segment 22 to facilitate coupling to an auxiliary device such as a syringe and/or a vacuum or aspiration source (not shown). The catheter hub 12 further may include a strain relief 24, which is positionable over a segment of the catheter member 14.

The catheter member 14 has a proximal end 26 and a leading catheter end segment 28. The system 1 may further includes a fluid source 34 such as saline or any other atraumatic fluid which may be fluidly coupled to the third port 20 of the catheter hub 12.

The catheter member 14 is dimensioned to access distal reaches of the vasculature and has sufficient flexibility to track along the guidewire 100, which is previously introduced within the vasculature. The catheter member 14 may be monolithically formed or may include multiple elements or tubes assembled and connected to the catheter hub 12. Varying segments of flexibility may be incorporated within the catheter member 14. For example, the catheter member 14 may have a relatively stiff segment adjacent the proximal end 26 and less stiff regions toward the leading end 28. The catheter member 14 may include defined regions or segments of flexibility or may gradually transition from a stiffer region to a less stiff region. The catheter member 14 may include a braid, a hypotube fabricated from materials including stainless steel, nitinol, nitinol alloys, or combinations thereof and/or a reinforced polymer tube. The braid may be fabricated from nitinol and have a continuous pitch, or include multiple sections with different winding pitches. Marker bands (not shown) may be embodied within the catheter member 14 adjacent the leading end segment 28 to assist in visualization of the catheter member 14 during implantation within the vasculature.

The guidewire 100 may be any conventional guidewire. In accordance with one application of the present disclosure, the maximum outer diameter of the guidewire ranges from about 0.008 inches (0.20 millimeters) to about 0.018 inches (0.46 millimeters). These diameters are standard for guidewires used, e.g., in a neurovascular procedure. Other diameters are contemplated for cardiovascular, peripheral vascular and gastrointestinal applications. The diameter of the guidewire may remain relatively constant over a major portion of the length of the guidewire. In the alternative, the leading or distal end incorporates a generally tapered or narrowed configuration to permit flexure while navigating the tortuous vasculature. The guidewire 100 may include a number of tapered segments, which may or may not be continuous. The length of the guidewire 100 may range from about 30 (760 millimeters) to about 400 inches (10,165 millimeters). Other lengths are also contemplated.

Referring now to FIGS. 2 and 3, in conjunction with FIG. 1, a first guidewire lumen 30 extends the length of the catheter member 14 and is in communication with the first port 16 for reception and passage of the guidewire 100. The third port 20 may be in fluid communication with the guidewire lumen 30. The catheter member 14 may define a device lumen 32 in communication with the second port 18 for passage of an interventional device.

Referring now to FIG. 4, in conjunction with FIGS. 1 and 2, one embodiment for securing the guidewire 100 to the catheter 10 to provide steering or deflecting capabilities to the catheter 10 is illustrated. In accordance with this embodiment, the system further includes a fluid source 34 such as saline or any other atraumatic fluid which may be fluidly coupled to the third port 20 of the catheter hub 12. The catheter member 14 includes a compressible clamp such as a grommet 36 positionable within the guidewire lumen 30 adjacent a leading catheter end segment 28 of the catheter member 14. The grommet 36 may be formed of any compressible resilient material including foam, a gel material, polyisoprene or the like. The grommet 36 defines an opening 40 to permit passage of the guidewire 100 when the grommet 36 is in the position of FIG. 4. The catheter member 14 defines opposed internal surfaces 42 adjacent the leading end 28, which taper radially inwardly relative to the longitudinal axis "k" toward the leading end 28 of the catheter member 14. In the first position of the grommet 36 as depicted in FIGS. 2 and 4, the catheter 10 may track along the guidewire 100. This first position of the grommet 36 corresponds to the disengaged or released condition of the guidewire 100 relative to the catheter member 14.

Figure 5:
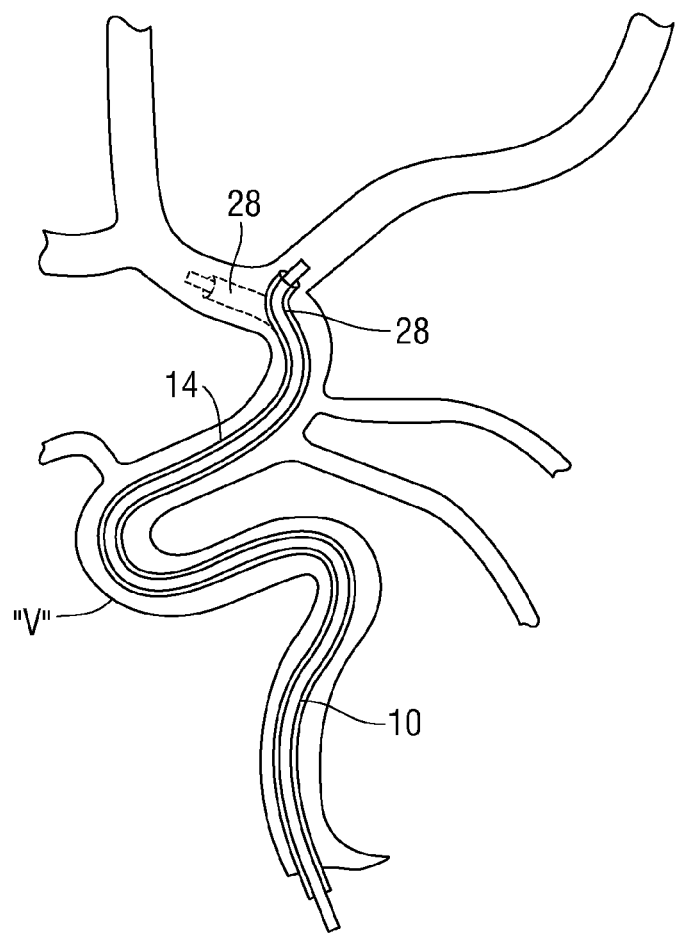
FIG. 5 is a view illustrating the catheter and the guidewire positioned within vasculature.

In use, and with reference to FIG. 5, which is a view representative of vasculature "v" of the subject, e.g., the neurovasculature, the guidewire 100 is positioned within the vasculature to access an intravascular site. The catheter 10 is advanced along the guidewire 100 within the guidewire lumen 30 of the catheter member 14 and through the opening 40 in the grommet 36. The catheter 10 is advanced along the guidewire 100 within the vasculature "v" with the leading catheter end segment 28 adjacent the targeted site.

With reference to FIGS. 5-7, in conjunction with FIG. 1, the fluid "f" from the fluid source 34 is delivered under pressure into the third port 20 to communicate with the guidewire lumen 30. In the alternative, the fluids "f" may be introduced within the first port 16 even in the presence of the guidewire 100 extending out from the first port 16. The fluid "f" drives the grommet 36 distally toward the leading catheter end segment 28 from the first position depicted in FIGS. 2 and 4 to the second position of the grommet 36 depicted in FIGS. 6 and 7. As the grommet 36 is driven toward the second position, the internal tapered surfaces 42 of the catheter member 14 cooperate to compress the grommet 36 such that the grommet 36 engages the guidewire 100 in secured relation therewith as best depicted in FIG. 7. The catheter member 14 may incorporate proximal and distal internal stops 44, 46 to limit movement of the grommet 36 within the guidewire lumen 30. The second position of the grommet 36 corresponds to the secured condition of the guidewire 100 relative to the leading catheter end segment 28. The fluids "f" may be continually supplied to the guidewire lumen 30 thereby maintaining continued pressure on the grommet 36. With the grommet 36 securely engaged to the guidewire 100 adjacent the leading catheter end segment 28 of the catheter member 14, the guidewire 100 is pulled in a proximal direction as shown by the directional arrows "m" of FIG. 8, which causes the leading catheter end segment 28 to correspondingly deflect relative to the longitudinal axis "k" in a direction "b". The degree of deflection may be controlled by the amount of retraction of the guidewire 100. FIG. 5 depicts, in phantom, the leading catheter end segment 28 in a deflected orientation within the vasculature "v". With the leading catheter end segment 28 in the desired orientation, an interventional device may be introduced through the second port 18 and into the device lumen 32 of the catheter member 14 to perform a desired intravascular procedure. Alternatively, controlling the degree of deflection enables the clinician to selectively engage and disengage the leading catheter end segment 28 to enable continued advancing movement of the catheter member 14 within the tortuous vasculature.

Once it is desired to disengage or release the leading catheter end segment 28 from the guidewire 100, the supply of fluids "f" introduced within the first lumen 30 is halted, relieving the distal pressure on the grommet 36. The guidewire 100 may be pulled in the proximal direction thereby displacing the grommet 36 toward the first position of FIGS. 2 and 4, allowing guidewire 100 to freely move within guidewire lumen 30 again. The catheter member 14 may incorporate proximal and distal stops 44, 46 to limit movement of the grommet 36 within the first lumen 30. The catheter 10 may be further advanced along the guidewire 100 or retracted as needed. Thus, the leading catheter end segment 28 may be selectively secured and released relative to the guidewire 100 via the aforedescribed movement of the grommet 36.

Figure 8:
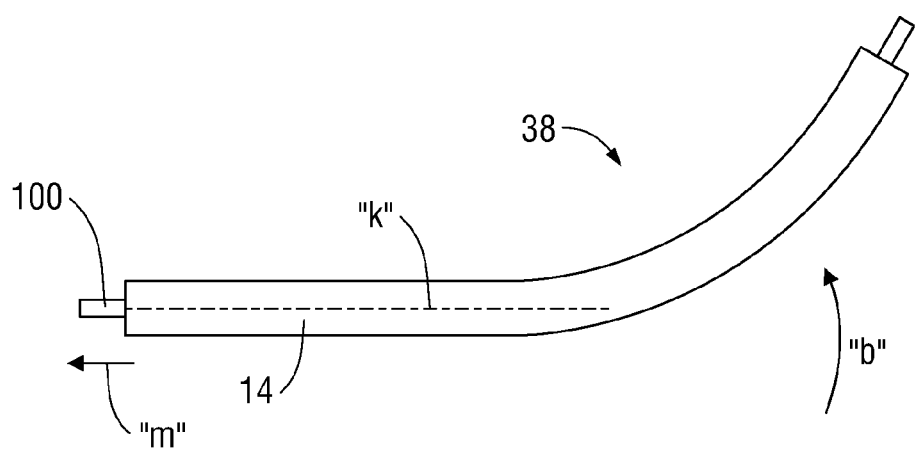
FIG. 8 is a view illustrating flexing of the leading catheter end segment upon movement of the guidewire in a longitudinal direction.

FIGS. 9-10 illustrate an alternate embodiment of the present disclosure. Catheter member 14 includes an expandable member 50 disposed within the first lumen 30. The expandable member 50 may be an inflatable balloon adapted to expand from the initial condition of FIG. 9 upon the passage of fluids from the fluid source 34 to within the internal chamber of the inflatable balloon 50, to the inflated condition illustrated in FIG. 10. An inflation conduit extends from the first or third port 16, 20 and is in fluid communication with the inflatable balloon. The conduit may be a separate inflation lumen 54 in the catheter member 14 as depicted in FIG. 9 in fluid communication with the interior of the inflatable balloon through port 56 extending through the wall 58 of the catheter member 14. In use, the catheter 10 is advanced along the previously positioned guidewire 100 within the vasculature. When the leading catheter end segment 38 is at the target site within the vasculature, inflation fluids are supplied from the fluid source 34 through either the first or third ports 16, 20 to pass through the fluid conduit such as the inflation lumen 54, for delivery through the port 56 and into the inflatable balloon to expand the inflatable balloon to the expanded condition depicted in FIG. 10. In the expanded condition, the inflatable balloon engages the guidewire 100 and secures the guidewire 100 relative to the inner surfaces 62 defining the first lumen 30 of the catheter member 14. Thereafter, the guidewire 100 is pulled in a proximal or trailing direction while the catheter 10 is held stationary causing the leading catheter end segment 38 to deflect as depicted in FIG. 8.

FIG. 11 depicts an alternate embodiment in which the separate inflation lumen 54 is eliminated. Fluid is conveyed to the inflatable balloon from the fluid source 34 through a tube 60 (shown schematically) which extends within the first lumen 30.

FIGS. 12-13 illustrate another embodiment incorporating a filament loop 70 for engaging the guidewire 100 to the catheter member 14. The filament loop 70 includes an elongated filament segment 72 and a loop segment 74. The filament segment 72 may extend through a third lumen 76 of the catheter member 14 or alternatively extend through the device lumen 32 thereby obviating the need for the third lumen 76. The loop segment 74 is positioned within or in general alignment with the first lumen 30 and extends through the interior wall 78 of the catheter member 14 for reception within the third lumen 76. The filament loop 70 may include a sliding knot or lasso forming the loop segment 74 which can be tied about the guidewire 100 by applying tension to the filament segment 72. Various known suture-lassoing techniques may be incorporated into the filament loop 70. In use, the guidewire 100 is advanced though the vasculature. The catheter member 14 is tracked along the guidewire 100 with the guidewire 100 passing through the guidewire lumen 30. When the guidewire 100 has been threaded through the loop segment 74, the filament segment 72 is pulled in the proximal direction (directional arrow "m" in FIG. 13). The loop segment 74, which incorporates the sliding knot or a running noose, grasps the guidewire 100 drawing the guidewire 100 against the internal wall 78 of the catheter member 14. In this condition, the guidewire 100 is secured relative to the catheter member 14. The guidewire 100 is moved in the proximal direction causing deflection of the leading catheter end segment 28 in a similar manner discussed hereinabove. In an alternate approach, the guidewire 100 may be secured with the filament loop 70 relative to the catheter member 14 prior to insertion of the guidewire 100 and the catheter member 14 within the vasculature, and the combined unit simultaneously advanced within the vasculature.

FIGS. 14-15 illustrate another embodiment of the present disclosure. In accordance with this embodiment, the catheter member 14 includes guidewire lumen 80, a device lumen 82 and a third lumen 84. The third lumen 84 is dimensioned to receive a drive element 86, which is adapted to reciprocate in a longitudinal direction within the third lumen 84. An actuator 88 may be connected to the proximal end of the drive element 86 for manual manipulation by the clinician to cause corresponding longitudinal movement of the drive element 86. The internal surfaces defining the third lumen 84 include a generally tapered surface 90 adjacent the catheter leading catheter end segment 92. In use, the guidewire 100 is positioned within the vasculature and the catheter member 14 is tracked along the guidewire 100 with the guidewire 100 passing through the guidewire lumen 80. When it is desired to engage the guidewire 100 to the leading catheter end segment 92, the drive element 86 is advanced from the first position depicted in FIG. 14 to the second position depicted in FIG. 15. Upon traversing the tapered surface 90, the leading end of the drive element 86 deflects towards the guidewire lumen 80, which causes the internal wall 94 of the lumen 80 to correspondingly deflect and drive the guidewire 100 against the opposed internal wall 96 of the first lumen 80. In this position, the guidewire 100 is wedged between the opposed internal walls 94, 96 and secured relative to the catheter member 14. The guidewire 100 may be moved in the trailing direction to accordingly deflect the leading catheter end segment 92 in a similar manner shown in FIG. 8. To release the guidewire 100, the actuator 88 and the drive element 86 are moved in the proximal direction causing the leading end of the drive element 86 to return to its first position, thereby permitting the internal wall 94 to return to its first position depicted in FIG. 14.

FIGS. 16-17 illustrate another embodiment of the present disclosure. In accordance with this embodiment, the catheter member 14 includes guidewire lumen 120, a device lumen 122 and a third lumen 124. The third lumen 124 includes an electromagnet 126 adjacent the leading catheter end segment 128. The electromagnet 126 may be powered by an energy source 130 in communication with the electromagnet 126 via electrical wire 132 extending from the energy source 130 through the third lumen 124. Alternatively, the electromagnet 126 may be powered via wireless technology. The guidewire 100 may be fabricated at least in part of ferromagnetic material such as steel, nitinol or other suitable ferromagnetic metals or polymers. In the initial unactuated condition of the electromagnet 126, the guidewire 100 may traverse the first lumen 120. Upon actuation of the electromagnet 126, the magnetic forces "f" thereby generated, will draw or deflect the guidewire 100 toward the electromagnet 126 as depicted in FIG. 17. In this position, a segment of the guidewire 100 is secured against the internal wall 130 separating the guidewire lumen 120 and a third lumen 124.

In use, the guidewire 100 is positioned within the vasculature and the catheter member 14 is tracked along the guidewire 100 with the guidewire 100 passing through the guidewire lumen 120. When it is desired to secure the guidewire 100 to the leading catheter end segment 128, the electromagnet 126 is actuated. The magnetic forces "f" causes deflection of the guidewire 100 towards the third lumen 124 securing guidewire 100 to the internal wall 130 and the electromagnet 126. The guidewire 100 may then be moved in the proximal direction to deflect the leading catheter end segment 128 in the same manner as shown in FIG. 8. To release the guidewire 100, the electromagnet 126 may be deactivated. The electromagnet 126 may be selectively activated and deactivated to provide selective engagement of the guidewire 100 to the leading catheter end segment 128. In embodiments, the electromagnet 126 may be replaced with a permanent magnet.

Figure 18:
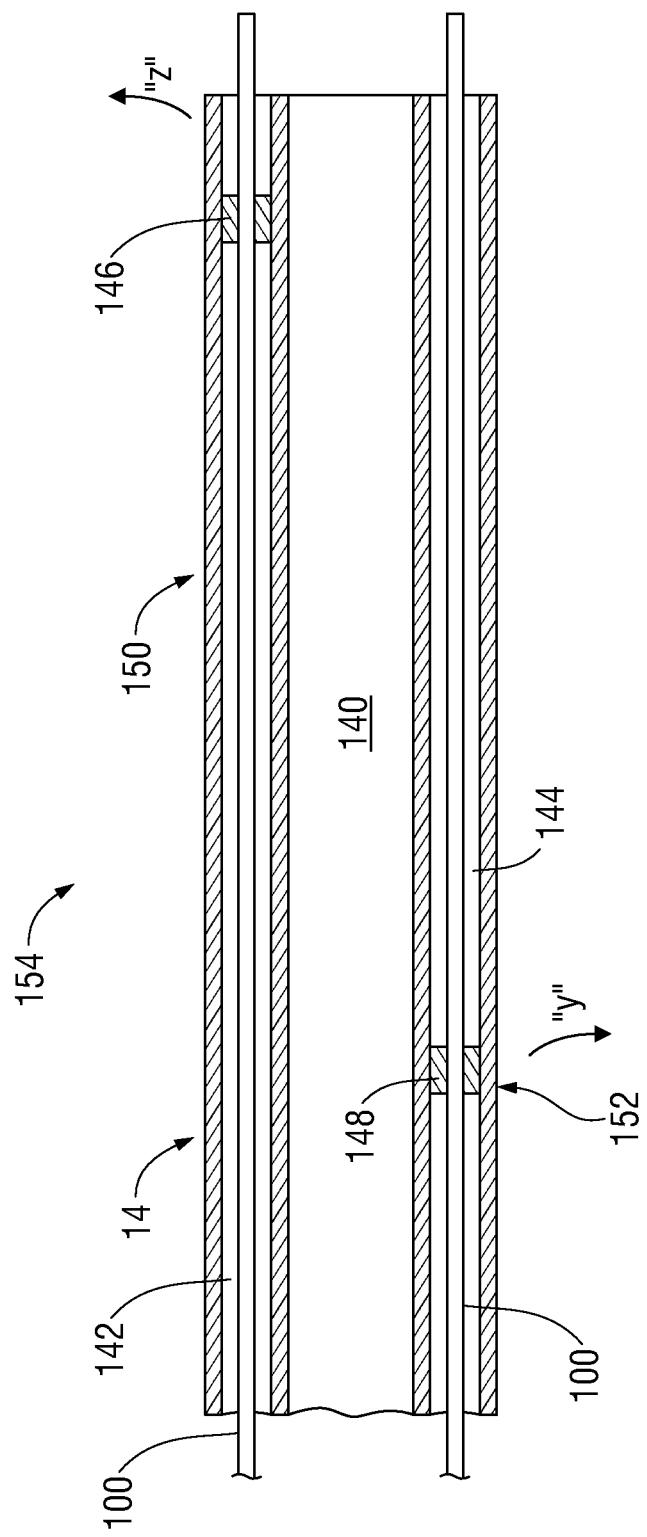
FIG. 18 is a side cross-sectional view of another embodiment of the catheter member incorporating first and second guidewires and corresponding first and second fastening structures for securing proximal and distal sections of leading catheter end segment of catheter system shown in FIG. 1.

FIG. 18 illustrates another embodiment of the present disclosure. In accordance with this embodiment, the catheter 14 includes three lumens, namely, device lumen 140 and first and second guidewire lumens 142, 144. The first and second guidewire lumens 142, 144 each may receive a guidewire 100. Each guidewire lumen 142, 144 also includes fastening structures, identified schematically as reference numerals 146, 148, respectively, for selectively engaging the guidewires 100. The fastening structure may include any of the aforedescribed arrangements described in connection with the embodiments of FIGS. 1-17. With the dual guidewire and fastener arrangement, different sections 150, 152 of the leading catheter end segment 154 may be secured and thus selectively deflected through corresponding movement of the guidewires 100 within the guidewire lumens 142, 144. For example, during the procedure, the clinician may desire to initially deflect the distal section 150 of the leading catheter end segment 154. The fastening structure 146 associated with the distal section 150 is activated securing the guidewire 100 relative to the distal most section 150. The distal section 150 is then deflected in the aforedescribed manner. When it is desired to deflect the second or proximal section 152 of the leading catheter end segment 154, the fastener structure 148 is activated securing the guidewire 100 adjacent this section 152. The guidewire 100 is manipulated to deflect the proximal section 152. In embodiments, the proximal and distal sections 152, 150 may be deflected in different, e.g., opposed directions relative to the longitudinal axis as depicted by the directional arrows "y", "z". In other embodiments, the proximal and distal sections 152, 150 may be deflected in the same direction. Other arrangements are also envisioned.

Figure 19:
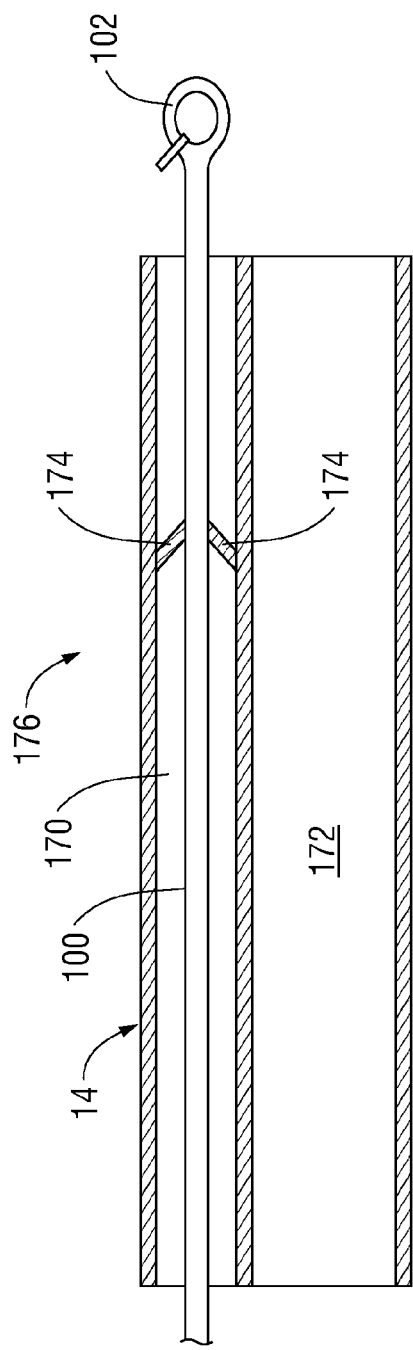
FIG. 19 is a side cross-sectional view of another embodiment of the catheter member incorporating a looped segment of the guidewire and depicting a release condition of the guidewire.
Figure 20:
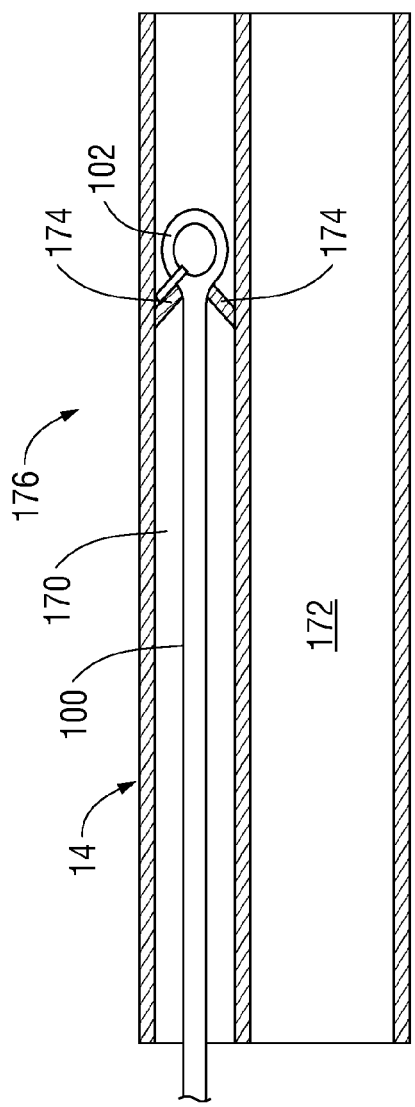
FIG. 20 is a view similar to the view of FIG. 19 illustrating the looped segment engaged with at least one locking detent of the catheter member depicting a secured condition of the guidewire.

FIGS. 19-20 illustrate another embodiment of the present disclosure. In accordance with this embodiment, the catheter member 14 includes guidewire lumen 170 and device lumen 172. The guidewire 100 may have a looped segment 102 at its distal end. The looped segment 102 may be formed and tied off by the clinician at the treatment site. The catheter member 14 may further include at least one or more inwardly depending detents 174 within the guidewire lumen 170. The locking detents 174 may be molded with the catheter member 14 during manufacture or be a separate component(s) secured to the catheter member 14 through adhesives and/or cements. In use, the catheter 14 is advanced along the guidewire 100. When it is desired to deflect the leading catheter end segment 176, the guidewire 100 is retracted or pulled in a proximal direction until the looped segment 102 engages the detents 174 whereby upon engagement therewith, the looped segment 102 and the catheter 100 are secured relative to the leading catheter end segment 176, i.e., achieving a secured condition depicted in FIG. 19. Further movement of the guidewire 100 in a proximal direction when in the secured condition will deflect the leading catheter end segment 176 in the manner discussed hereinabove.

Figure 21:
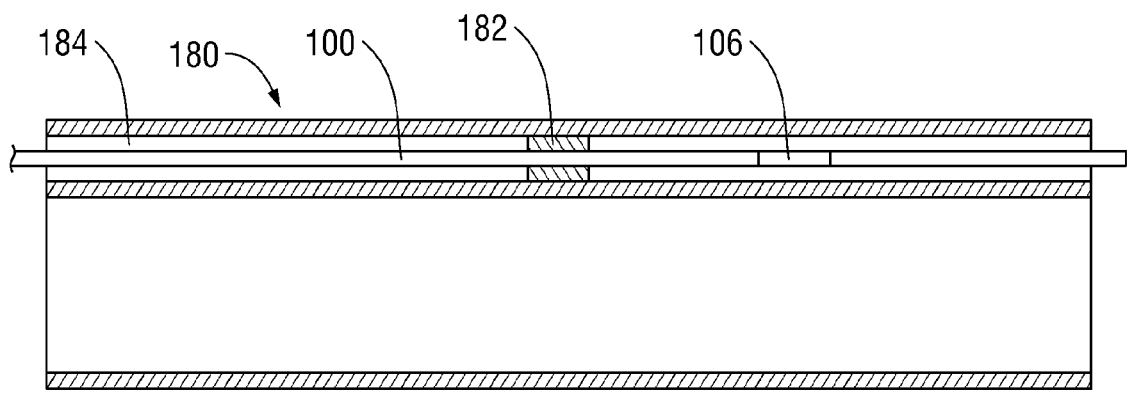
FIG. 21 is a side cross-sectional view of another embodiment of the catheter member incorporating a guidewire having a lock element and the catheter having corresponding lock structure, and depicting a release condition of the guidewire.
Figure 22:
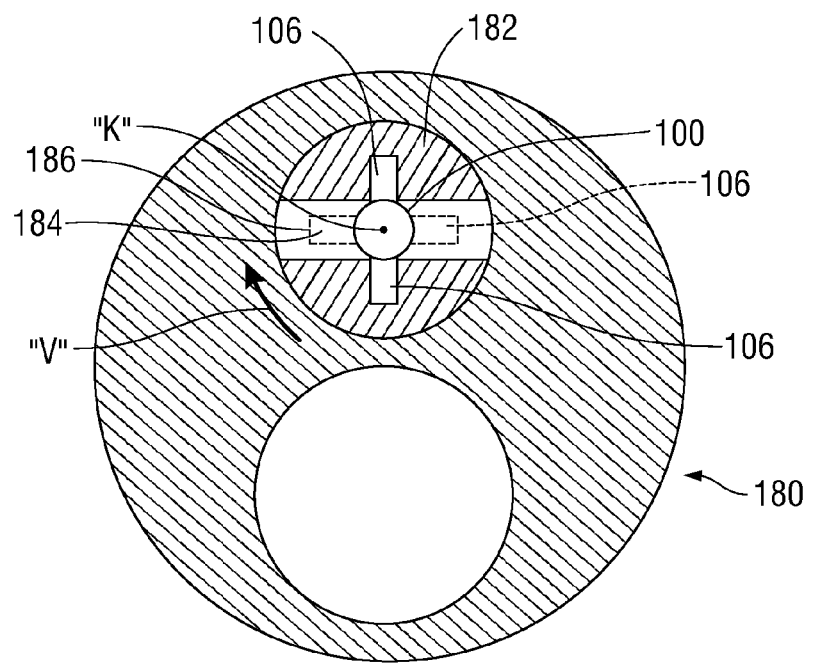
FIG. 22 is an enlarged axial cross-sectional view illustrating the guidewire rotated relative to the catheter member whereby the lock element of the guidewire and the lock structure of the catheter member are engaged depicting a secured condition of the guidewire.

FIGS. 21-22 illustrate another embodiment of the present disclosure. In accordance with this embodiment, the leading catheter end segment 180 includes internal locking structure 182 which may be at least one wall, detent, and/or surface of predefined geometry extending within the lumen 184 of the leading catheter end segment 180. The guidewire 100 includes locking element 106 which generally corresponds to the opening 186 in the predefined geometry of the locking structure 182. To initially advance the guidewire 100 relative to the leading catheter end segment 180, the lock element 106 is generally aligned with the opening 186 of the locking structure 182 to permit passage of the guidewire 100 through the lumen 184. When it is desired to secure the guidewire 100 relative to the leading catheter end segment 180, the guidewire 100 is rotated through an arc of rotation "v", e.g., 90 degrees about the longitudinal axis "k", to displace the lock element 106 relative to the locking structure as shown in FIG. 22 (note the release or aligned position of the lock element 106 relative to the locking structure 182 is shown in phantom). In this secured position, the leading catheter end segment 180 may be deflected through longitudinal movement of the guidewire 100 as discussed hereinabove. When it is desired to release the guidewire 100, the guidewire may be rotated 90 degrees in the opposite direction to align the lock element 106 with the opening 186 in the locking structure 182 (760 millimeters) 100 and the leading catheter end segment 180. The guidewire 100 may be selectively secured and released relative to the leading catheter end segment 180 during use of the system 1.

Figure 23:
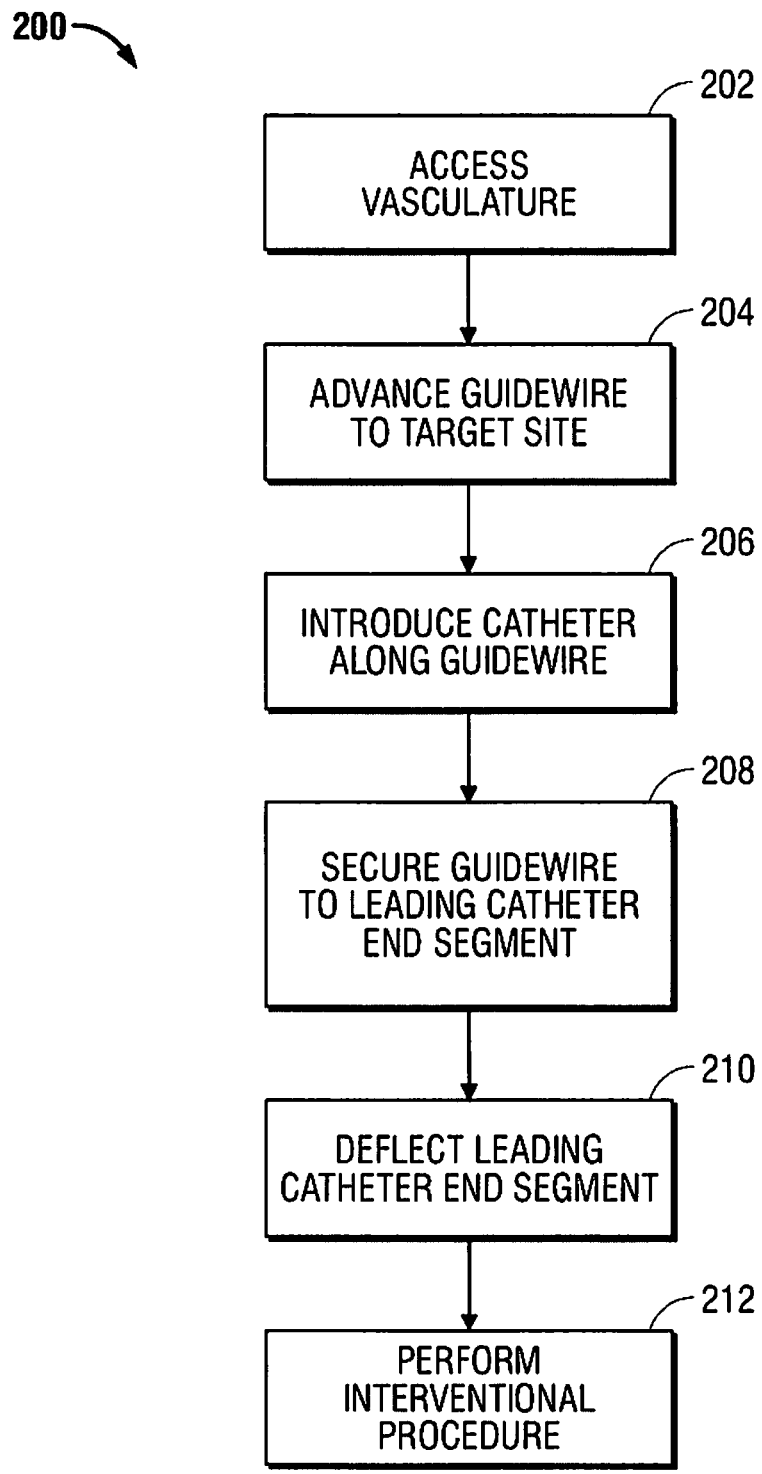
FIG. 23 is a flow chart illustrating an exemplary use of the system in an intravascular procedure.

FIG. 23 is a flow chart depicting an exemplary method of use of the system 1 in performing a surgical procedure and In accordance with one exemplary procedure 200, the vasculature is accessed (STEP 202) by, e.g., introducing a hollow needle into an artery or vein via a percutaneous procedure. The guidewire is introduced within the needle and advanced to a location proximate a targeted site. (STEP 204). The catheter 10 is then introduced and advanced along the guidewire 100 (STEP 206) to position the leading catheter end segment 28, 38, 92, 128, 154, 176, 180 adjacent the targeted site. Any of the aforedescribed selective engagement mechanisms may be utilized to secure the guidewire 100 relative to the leading catheter end segment 28, 38, 92, 128, 154, 176, 180 of the catheter member (STEP 208). The leading catheter end segment 28, 38, 92, 128, 154, 176, 180 is deflected by pulling on the guidewire in a proximal direction (STEP 210) to facilitate further advancement of the catheter 10. It is envisioned that the leading catheter end segment 28, 38, 92, 128, 154, 176, 180 may be selectively secured and released relative to the guidewire 100 during advancement. An interventional procedure is performed (STEP 212) by introducing a device through a device lumen of the catheter to access vasculature and treatment sites. Examples of procedures contemplated include, but are not limited to introducing a stent, deploying, a flow diverter device across an arteriovenous malformation (AVM) or an aneurysm, deploying a flow restoration device to capture an occlusion, and/or introducing embolic coils or an embolic solution into an aneurysm.

It is to be appreciated that the disclosure has been described hereinabove with reference to certain examples or embodiments of the disclosure but that various additions, deletions, alterations and modifications may be made to those examples and embodiments without departing from the intended spirit and scope of the disclosure. For example, any element or attribute of one embodiment or example may be incorporated into or used with another embodiment or example, unless otherwise specified to do so would render the embodiment or example unsuitable for its intended use. In addition, the catheter member 14 may be a single lumen catheter where each of the disclosed embodiments of locking mechanisms or fastener structure is disposed within the single lumen. All reasonable additions, deletions, modifications and alterations are to be considered equivalents of the described examples and embodiments and are to be included within the scope of the following claims.

What is claimed is:

1. A catheter system, which comprises:
   an elongate catheter defining a longitudinal axis and defining a lumen extending at least partially therethrough, the catheter comprising a leading catheter end segment;
   a guidewire positionable within the lumen of the catheter, the guidewire and the catheter being adapted for relative movement; and
   a fastening structure within the lumen of the elongate catheter and supported adjacent the leading catheter end segment, the guidewire extending through the fastening structure, wherein the fastening structure is dimensioned to selectively engage the guidewire to secure the guidewire with respect to the leading catheter end segment, and wherein the fastening structure is positioned within the elongate catheter such that when the fastening structure is engaged with the guidewire, movement of the guidewire causes deflection of the leading catheter end segment with respect to the longitudinal axis.

2. The catheter system according to claim 1 wherein the fastening structure includes a clamp adjacent the leading catheter end segment, the clamp movable between a rest position corresponding to a release condition of the guidewire and an actuated position corresponding to a secured condition of the guidewire where the clamp engages the guidewire in the lumen in secured relation therewith.

3. The catheter system according to claim 2 wherein the clamp is at least partially disposed within the lumen of the catheter when the clamp is in the actuated position.

4. The catheter system according to claim 3 wherein the clamp is a grommet, the grommet defining a passage for reception of the guidewire, the grommet being at least partially compressible to engage the guidewire upon movement to the actuated position.

5. The catheter system according to claim 4 wherein the grommet is adapted to move within the lumen from a first longitudinal position to a second longitudinal position in response to introduction of fluids within the lumen.

6. The catheter system according to claim 5 wherein the catheter includes internal tapered surfaces adjacent the lumen, the tapered surfaces cooperating with the grommet during movement thereof to the second longitudinal position to compress the grommet onto the guidewire.

7. The catheter system according to claim 5 including a source of pressurized fluids in fluid communication with the lumen.

8. The catheter system according to claim 1 wherein the fastening structure includes a filament member extending along the catheter and defining a loop segment, the loop segment dimensioned to receive the guidewire to secure the guidewire with respect to the leading catheter end segment.

9. The catheter system according to claim 8 wherein the loop segment includes a lasso.

10. The catheter system according to claim 1 wherein the catheter includes a device lumen dimensioned for reception of an interventional device.

11. The catheter system according to claim 1 wherein the guidewire is adapted for one of rotational or radial movement relative to the catheter to secure the guidewire with respect to the leading catheter end segment.

12. The catheter system according to claim 1 wherein the lumen comprises a first lumen, the guidewire comprises a first guidewire, the fastening structure comprises a first fastening structure, and the leading catheter end segment includes first and second catheter sections, and wherein the first fastening structure is configured to secure the first guidewire with respect to the first catheter section such that when the first fastening structure is engaged with the first guidewire, movement of the first guidewire causes deflection of the first catheter section, the catheter further defining a second lumen, and the catheter system further comprising:
   a second guidewire positionable within the second lumen of the catheter, each of the first and second guidewires being adapted for relative movement within the respective first and second lumens; and
   a second fastening structure dimensioned to selectively engage the second guidewire to secure the second guidewire with respect to the second catheter section, and wherein the second fastening structure is positioned within the elongate catheter such that when the second fastening structure is engaged with the second guidewire, movement of the second guidewire causes deflection of the second catheter section.

13. The catheter system according to claim 12 wherein the first catheter section is adapted to deflect in a first radial direction with respect to the longitudinal axis and the second catheter section is adapted to deflect in a second radial direction with respect to the longitudinal axis.

14. The catheter system according to claim 13 wherein the first radial direction is different from the second radial direction.

15. The catheter system according to claim 1 wherein the guidewire includes a looped segment, and the fastening structure includes at least one detent depending into the lumen, the detent positioned to engage the looped segment of the guidewire to secure the guidewire with respect to the leading catheter end segment.

16. The catheter system according to claim 1 wherein the fastening structure includes a locking structure of predefined geometry within the lumen and the guidewire includes a locking element, the locking element adapted to move between a release condition and a secured condition with respect to the leading catheter end segment through relative rotation of the guidewire and the leading catheter end segment about the longitudinal axis, wherein in the secured condition, the guidewire is secured with respect to the leading catheter end segment.

17. The catheter system according to claim 1, wherein the fastening structure is dimensioned to selectively directly engage the guidewire to secure the guidewire with respect to the leading catheter end segment such that when the fastening structure is engaged with the guidewire, movement of the guidewire causes deflection of the leading catheter end segment with respect to the longitudinal axis.

18. A medical method, comprising:
introducing a guidewire within vasculature of a subject;
advancing a catheter along the guidewire;
securing the guidewire relative to a leading end segment of the catheter, wherein securing the guidewire comprises securing the guidewire with a fastening structure within a lumen of the catheter and supported adjacent the leading catheter end segment, the guidewire extending through the fastening structure, wherein the fastening structure is dimensioned to selectively engage the guidewire to secure the guidewire with respect to the leading catheter end segment, and wherein the fastening structure is positioned within the elongate catheter such that when the fastening structure is engaged with the guidewire, movement of the guidewire causes deflection of the leading catheter end segment with respect to the longitudinal axis; and
manipulating the guidewire to cause deflection of the leading end segment of the catheter.

19. The medical method according to claim 18 wherein securing the guidewire is performed subsequent to advancing the catheter.

20. The medical method according to claim 18 wherein securing the guidewire includes selectively securing and releasing the guidewire relative to the leading end segment of the catheter.

21. The medical method according to claim 18 further comprising performing an interventional procedure.

22. The medical method according to claim 21 wherein performing the interventional procedure includes introducing a medical device within the catheter.

* * * * *